United States Patent
Reischl

(10) Patent No.: US 7,455,761 B2
(45) Date of Patent: Nov. 25, 2008

(54) NITROGEN OXIDE SENSOR WITH ATTENUATED OXYGEN DEPENDENCE OF THE NOX SIGNAL

(75) Inventor: Rolf Reischl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 871 days.

(21) Appl. No.: 10/489,798

(22) PCT Filed: Aug. 2, 2002

(86) PCT No.: PCT/DE02/02860

§ 371 (c)(1),
(2), (4) Date: Oct. 13, 2004

(87) PCT Pub. No.: WO03/027655

PCT Pub. Date: Apr. 3, 2003

(65) Prior Publication Data

US 2005/0029127 A1 Feb. 10, 2005

(30) Foreign Application Priority Data

Sep. 17, 2001 (DE) ................. 101 45 804

(51) Int. Cl.
*G01N 27/407* (2006.01)
(52) U.S. Cl. .................. 205/781; 204/406; 204/425
(58) Field of Classification Search ............ 204/424, 204/425, 426, 406; 205/781, 784.5
See application file for complete search history.

(56) References Cited

U.S. PATENT DOCUMENTS

2001/0000598 A1 5/2001 Miyata et al.

2001/0039825 A1 11/2001 Kurokawa et al.

FOREIGN PATENT DOCUMENTS

| DE | 199 12 102 | 10/2000 |
|---|---|---|
| DE | 199 62 912 | 7/2001 |
| DE | 101 16 184 | 10/2002 |
| DE | 101 21 771 | 11/2002 |
| EP | 0 878 709 | 11/1998 |
| EP | 0 924 514 | 6/1999 |
| JP | 2000 097 905 | 4/2000 |

OTHER PUBLICATIONS

Machine translation of JP 2000-97905, Apr. 2000.*

* cited by examiner

*Primary Examiner*—Kaj K Olsen
(74) *Attorney, Agent, or Firm*—Kenyon & Kenyon LLP

(57) ABSTRACT

In a method and with a circuit for operating a nitrogen oxide sensor for determining the nitrogen oxide (NOx) concentration in a gas mixture, in particular in post-treatment of an automotive exhaust, an electric pumping voltage (U_APE, IPE) which induces a pumping current (I_pump) being applied between an internal pump electrode (IPE) and an external pump electrode (APE) of a pumping cell, by which a constant oxygen partial pressure is established in a first test gas space by pumping oxygen in or out, the pumping voltage (U_APE,IPE) being regulated so that a constant voltage value is established at electrodes of a concentration cell, a NOx-sensitive third electrode situated in a second test gas space being operated as the second pumping cell in which a limit pumping current is established, indicating the NOx concentration, in order to minimize the influence of oxygen on the nitrogen oxide signal measured, the pumping current (I_pump) is switched off or reduced in a controlled manner within a measurement time window (T_Mess) and the NOx concentration is determined within the measurement time window (T_Mess).

16 Claims, 6 Drawing Sheets

NITROGEN OXIDE SENSOR WITH ATTENUATED OXYGEN DEPENDENCE OF THE NOX SIGNAL

FIELD OF THE INVENTION

The present invention relates in general to exhaust-gas aftertreatment, in particular using lambda regulation in fuel-driven motor vehicles, and in particular to a method and a circuit for operating a nitrogen oxide sensor suitable for use with such a lambda regulation for determining the nitrogen oxide concentration in an exhaust-gas mixture.

BACKGROUND INFORMATION

Lambda regulation in combination with a catalytic converter is the most effective method today for purifying the exhaust from an internal combustion engine. Very low emission levels are achievable only by combination with the ignition and injection systems available today. Using a three-way or selective catalytic converter is particularly effective. This type of catalytic converter is capable of achieving greater than 98% degradation of hydrocarbons, carbon monoxide, and nitrogen oxides if the engine is operated at LAMBDA=1 in a range of approximately 1% around the stoichiometric air/fuel ratio. LAMBDA is an indicator of the deviation of the actual air/fuel mixture from LAMBDA=1, corresponding to a weight ratio of 14.7 kg/air to 1 kg/gasoline, as required theoretically for complete combustion, i.e., LAMBDA is the ratio of air mass supplied to theoretical air demand.

In lambda regulation, a measurement is performed on the particular exhaust and the quantity of fuel supplied is corrected immediately according to the results of this measurement via the injection system, for example. The measuring sensor is a lambda probe which shows a sudden change in voltage at precisely LAMBDA=1 and then delivers a signal indicating whether the mixture is richer or leaner than LAMBDA=1. The efficiency of the lambda probe is based on the principle of a galvanic oxygen concentration cell having a solid-state electrolyte.

Known lambda probes are two-point probes which operate by the Nernst principle using a Nernst cell. The solid-state electrolyte is composed of two interfaces separated by a ceramic. The ceramic material used becomes conducting for oxygen ions at approximately 350° C., so a Nernst voltage is generated when different oxygen levels prevail on the two sides of the ceramic between the interfaces. This voltage is a measure of the difference in oxygen levels on the two sides of the ceramic. Since the residual oxygen content of the exhaust of an internal combustion engine depends greatly on the air/fuel ratio the mixture supplied to the engine, it is possible to use the oxygen content of the exhaust as a measure of the actual prevailing air/fuel ratio.

With broadband probes, the measuring sensor is designed as a broadband sensor having solid electrolyte layers and a plurality of electrodes. Such a design is described in German Published Patent Application No. 199 12 102, in particular on pages 8 and 9 and in FIG. 1, to which reference is made to the full extent in the present context. These electrodes are also diagramed schematically in FIG. 1, which is described in detail below. A portion of these electrodes forms a pumping cell in this sensor, while another portion forms what is called a concentration cell. Furthermore, a first test gas space is formed by the solid electrolyte layers.

A pumping voltage U_APE,IPE is applied to the electrodes of the pumping cell (FIG. 1); a constant oxygen partial pressure is established in the first test gas space by pumping oxygen in or out using this pumping voltage. The pumping voltage here is regulated so that a constant voltage of 450 mV is established on the electrodes of the concentration cell. This voltage corresponds to a value of LAMBDA=1. Another electrode situated in a second test gas space is operated with one of these electrodes as the second pumping cell. Because of the catalytic material, this additional electrode functions as a NOx-sensitive electrode on which NOx is reduced according to the reaction NO→½N$_2$+½O$_2$. At the same time, the above-mentioned reference electrode functions as the second pump electrode at which the oxygen pumped out of the second test gas space is released into the atmosphere. A limit current is thus established on the electrochemical cell, which functions as an additional pumping cell, and this limit current is picked up as a test signal which indicates the NOx concentration.

It should be pointed out that the diffusion barrier described in German Published Patent Application No. 199 12 102 need not necessarily be included, and eliminating this barrier actually greatly reduces the gas travel times.

The measuring sensor described here may be used as a nitrogen oxide (NOx) sensor or as a hydrocarbon (HC) sensor. In its function as a NOx sensor, the NOx test signal reveals a dependence on the particular oxygen partial pressure in the measurement cell. This influence is due mainly to electric interactions of the sensor electrodes occurring in the sensor ceramic. The main influence is based on the main pump distance shown in FIG. 1 between the external pump electrode (APE) and the internal pump electrode (IPE), with the electric current (5 mA to 10 mA) and thus its pumping level having to be taken into account accordingly at a variable oxygen content.

This O$_2$ influence is known to be compensated by electronic or computed addition or subtraction with an IPE current-dependent factor using suitable analyzer circuits, the gain of this compensation having to be set specifically for each individual sensor. Such a circuit for electronic compensation is shown in the block diagram in FIG. 1.

An object of the present invention is therefore to provide a method as defined in the preamble and a circuit which avoid the disadvantages mentioned above and minimize the above-mentioned influence of oxygen on the nitrogen oxide signal using the simplest possible technical means and the least expensive method possible.

The present invention is based on the idea of briefly suppressing the cause of the influence of oxygen on the nitrogen oxide signal, namely the main pumping current prevailing between the internal pump electrode (IPE) and the external pump electrode (APE), so that an uncorrupted NOx signal may be recorded during this period of time.

In a first variant according to the present invention, (main) pumping current I_pump is switched off, i.e., set at a value of 0, within a measurement time window T_mess. In a second variant, an IPE current control sets the main pumping current at a constant value>0 during measurement time window T_mess, so that although the influence of the main pumping current is not eliminated entirely, it is kept constant while the pumping level is reduced to a lesser extent and yet the amplitude of the oxygen concentration interference is reduced greatly.

In a preferred embodiment, measurement time window T_Mess is dimensioned so that the pumping current flowing between IPE and APE has already subsided within T_Mess and the increase in oxygen concentration due to the current switching off or current reduction has not yet reached the NOx electrode within T_Mess.

This above-mentioned intervention in the pumping current may be performed regularly at a repeat frequency, whereby the repeat frequency for the current switching off or current reduction is of such a dimension that the interference in the oxygen concentration has subsided again at the beginning of each subsequent IPE switching off or reduction. As an alternative, main pumping current I_pump may be switched off or reduced temporarily during operation of the nitrogen oxide sensor and a calibration performed then.

According to one exemplary embodiment, measurement time window T_Mess is in the range of 10-100 μsec, preferably 60 μsec, and the repeat frequency is in the range of 10-100 Hz, preferably 50 Hz.

DETAILED DESCRIPTION

Figure 1:
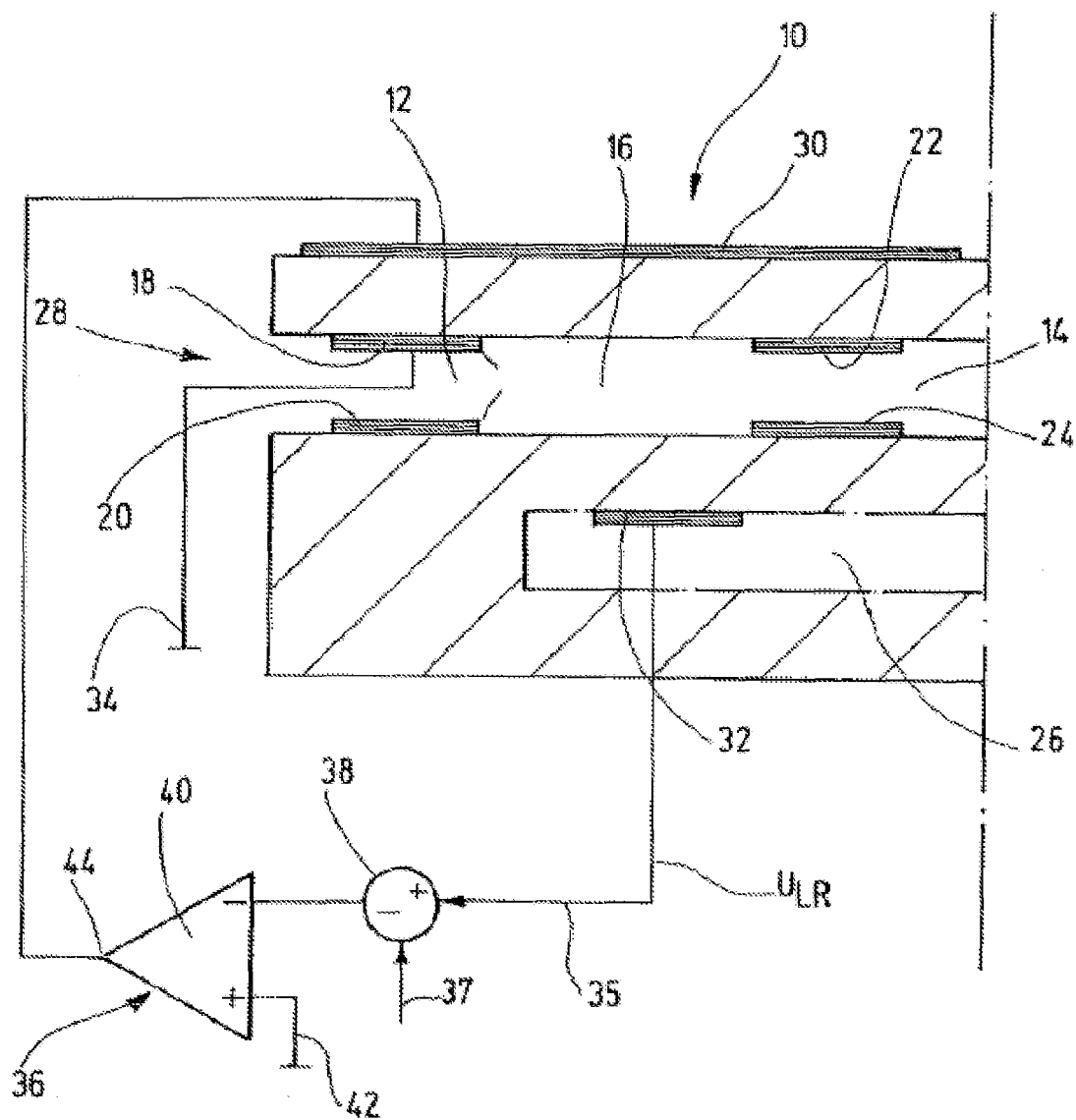
FIG. 1 shows the basic design of a main pump segment of a NOx sensor according to the related art.

FIG. 1 schematically shows the design of a main pump segment of a NOx sensor 10 known in the related art. Sensor 10 includes a first test gas space 12 which is connected to the test gas (here: exhaust). A first internal electrode 18, which functions as an internal pump electrode (IPE), and a second internal electrode 20 are situated in test gas space 12. Furthermore, a second test gas space 14 is connected to first test gas space 12, a third electrode (ME) 22 and a fourth electrode (NO) 24 being situated in this second test gas space.

A reference gas channel 26 is situated independently of two test gas spaces 12, 14, leading out of the body of sensor 10 at one end and connected to the atmosphere. Sensor 10 also has one or more gas inlet openings 28, which carry test gas into first test gas space 12.

Furthermore, an external electrode (APE) 30 which is situated on the external surface of a solid electrolyte layer (not shown) is exposed directly to the test gas. A fifth electrode (LR) 32 is also situated in reference gas channel 26, where it is exposed to the atmosphere; this electrode is referred to below as the air reference electrode. It should be pointed out that alternatively fifth electrode 32 may be exposed to the test gas.

In operation of the NOx sensor shown in FIG. 1, external electrode 30 and first internal electrode 18 are operated as pump electrodes of a first pumping cell. Second internal electrode 20 as a concentration cell is connected to fifth electrode 32, which functions as the reference electrode.

A pumping voltage U_APE,IPE is applied to electrodes 18, 30, establishing a constant oxygen partial pressure in first test gas space 12 by pumping oxygen in or out. Pumping voltage U_APE,IPE applied to electrodes 18, 30 is regulated so that a constant voltage of 450 mV, for example, is set on electrodes 20, 32 of the concentration cell. This voltage corresponds to LAMBDA=1.

With a lean test gas (LAMBDA>1), oxygen is pumped out of first test gas space 12 by the first pumping cell. With a rich test gas (LAMBDA<1), oxygen from the test gas is pumped into first test gas space 12. The choice of electrode material and/or a suitable pumping voltage U_APE,IPE ensures that no NOx is pumped out at electrodes 18, 20 when the first pumping cell 18, 30 pumps oxygen.

The test atmosphere, set at a constant oxygen partial pressure, goes through a connecting channel 16, which is indicated only schematically, into second test gas space 14. Third internal electrode (measuring electrode 'ME') 22, which is in second test gas space 14, is operated with fifth electrode 32 as a second pumping cell. Because of the catalytic material, fourth internal electrode 24 (here labeled as 'NO') acts as a NOx-sensitive electrode on which NOx is reduced according to the reaction NO $\rightarrow$ ½N$_2$+½O$_2$. At the same time, the reference electrode 32 cooperating with electrode 20 acts as a second pump electrode at which oxygen pumped out of second test gas space 14 is released into the atmosphere. A limit current indicating the NOx concentration is thus established on the electrochemical cell 22, 32, which functions as the other pumping cell, and is picked up as a test signal.

Furthermore, FIG. 1 illustrates the function of the main pump segment of NOx sensor 10. The configuration shown here has the function of keeping the oxygen concentration, i.e., the value of LAMBDA, at a constant value, e.g., LAMBDA=1, in first test gas space 12 on internal pump electrode 18. The value of LAMBDA in first test gas space 12 may be evaluated by the Nernst voltage occurring between internal pump electrode 18 and air reference electrode 32.

If internal pump electrode 18 is now set at ground potential 34, the value of LAMBDA occurring at internal pump electrode 18 may be represented by the electric voltage between air reference electrode 32 and ground 34. This value 35 forms the actual value of a controlled system 36 from which setpoint value U_lambda_setpoint 37 is subtracted by a summation element 38. The differential signal is sent to the negative input of a two-position controller 40 designed as a difference amplifier, in the present exemplary embodiment an operational amplifier having a gain>10,000. The reference input of two-position controller 40 is at ground 42. Output 44 of two-position controller 40 is connected to external pump electrode 30. Oxygen is pumped into or out of first test gas space 12 according to the size and sign of the difference between U_LR 35 and U_lambda_setpoint 37.

Figure 2:
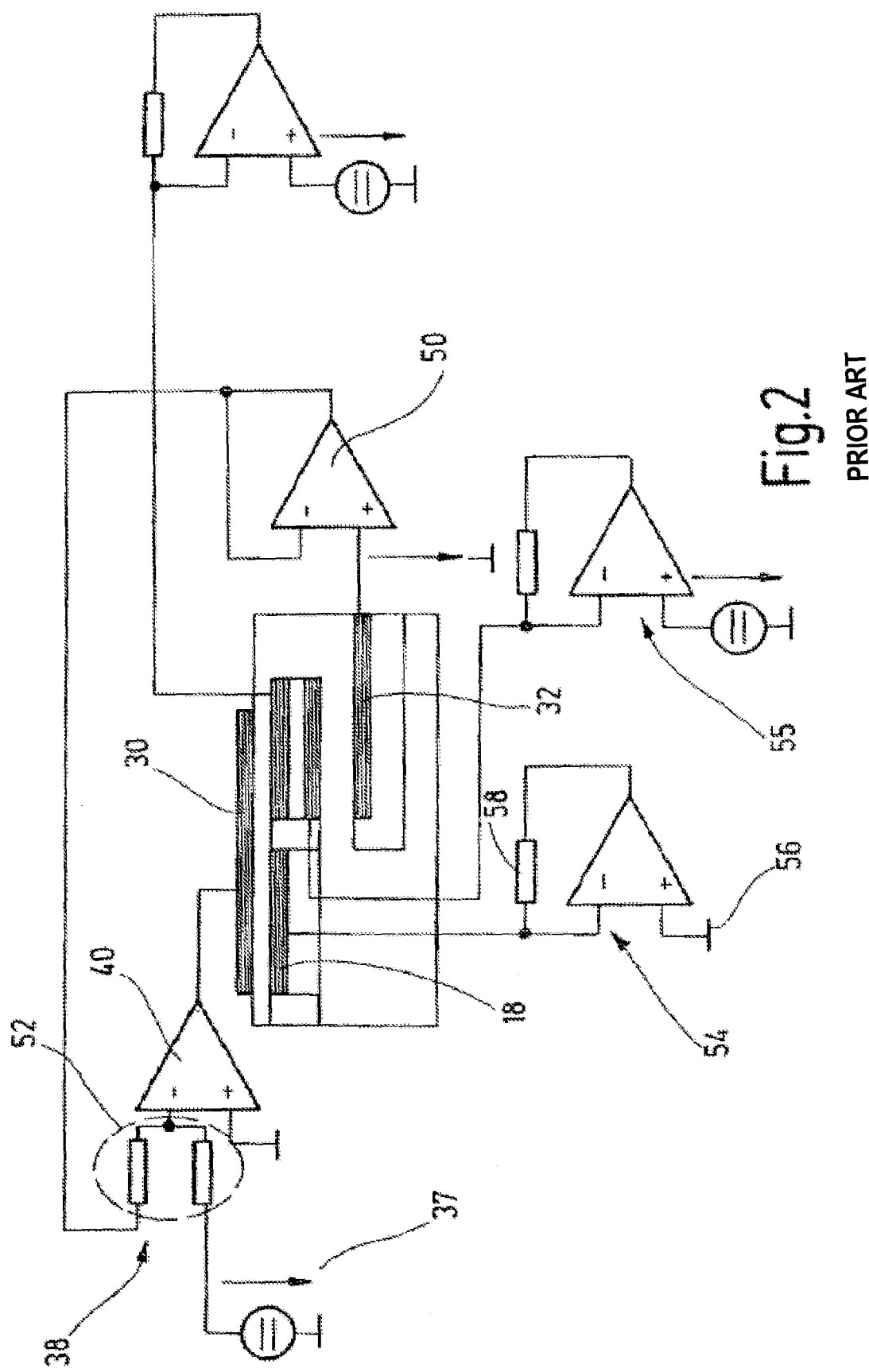
FIG. 2 shows a circuit configuration according to the related art for operation of the main pump segment illustrated in FIG. 1.

FIG. 2 shows circuitry implementing the configuration shown in FIG. 1. To avoid corrupting voltage U_LR 35 measured on air reference electrode 32 due to current flow, voltage U_LR 35 is transmitted via an isolation amplifier (OP3) 50 to summation point 38 at the negative input of two-position controller (OP5) 40. Setpoint value 37 is formed by a negative voltage, which is added to the actual value via a resistor network 52. Internal pump electrode 18 is applied to ground 56 via a guard amplifier 54. The output voltage of guard amplifier 54 represents pumping current I_IPE occurring between external pump electrode (APE) 30 and internal pump electrode (IPE), for which it thus holds that I_IPE=U_IPE/R1.

Figure 3:
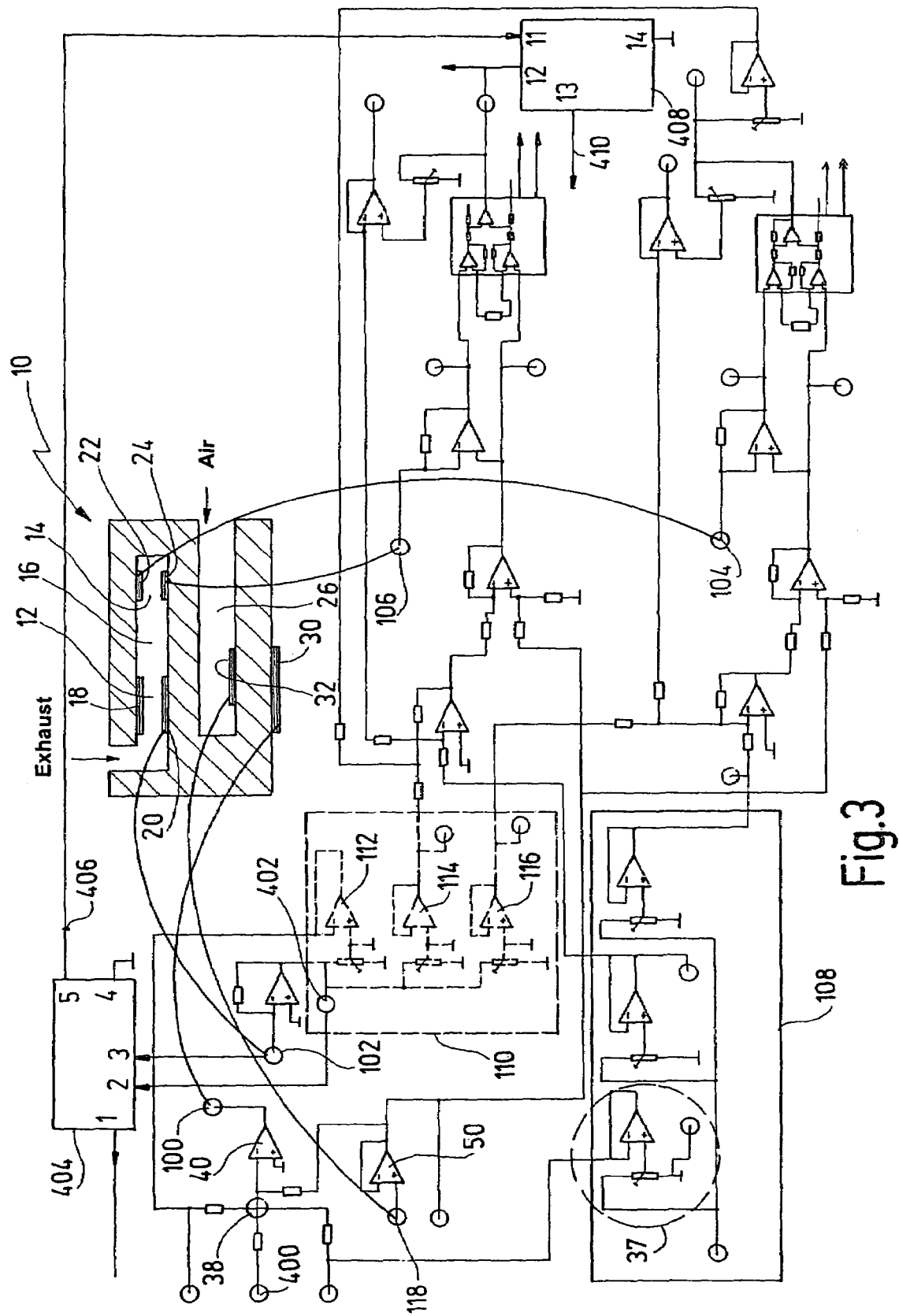
FIG. 3 shows an analyzer circuit according to the present invention for compensation of the oxygen dependence of a NOx sensor.

FIG. 3 shows an analyzer circuit according to the present invention for compensation of the oxygen dependence of a NOx sensor 10. This diagram shows that internal pump electrodes (IPE) 18, 20 are short-circuited, and together with external pump electrode (APE) 30 they are electrically connected via power supply lines to voltage supply terminals 100, 102 of the circuit shown. Corresponding terminals 104, 106 are provided for measuring electrode (ME) 22 and NOx-sensitive electrode (NO) 24.

Furthermore, the analyzer circuit has a first circuit part 108 which is provided for the basic equalization of sensor 10. Furthermore, a second circuit part 110, which is wired as an addition or subtraction stage, is also provided and is responsible for the oxygen compensation described above via an IPE current-dependent factor which is provided by a linear configuration of operational amplifiers 112, 114, and 116. The electronics depicted in FIG. 3 are also connected electrically to air reference electrode 32 via a terminal 118.

It should be pointed out that the analyzer circuit depicted in FIG. 3 also has some components that are known in the related art, in particular the compensation stage formed by operational amplifiers 112 through 116 for compensation of the $O_2$ influence with an IPE current-dependent factor, as already mentioned in conjunction with FIG. 1. The broken-line diagram of parts 112 through 116 is intended to indicate that these parts are not necessary at the present time.

According to the present invention, the analyzer circuit has an IPE interrupt module 404 connected via terminals 400, 402, and 102. Interrupt module 404 is also connected via a control line 406 to a NOx measured value acquisition module 408. IPE interrupt module 404 interrupts main pumping current I_pump, i.e., sets it at a value of zero, within a measurement time window T_Mess. As an alternative, it is also possible for IPE interrupt module 404 to set the main pumping current at a constant value>0 during measurement time window T_Mess, so that although the influence of the main pumping current is not eliminated entirely, it is kept constant while the pumping level is reduced to a lesser extent and yet the amplitude of the oxygen concentration interference is reduced greatly.

Measurement time window T_Mess is dimensioned so that pumping current I_pump flowing between IPE 18, 20 and APE 30 has already subsided within T_Mess and the increase in oxygen concentration due to the current switching off or reduction has not yet reached NOx electrode 24 within T_Mess.

In the exemplary embodiment, this change in pumping current I_pump is performed at a repeat frequency, whereby the repeat frequency for the current switching off or current reduction is of such a dimension that the interference in oxygen concentration has already subsided again at the beginning of each subsequent IPE switching off or reduction. Measurement time window T_Mess in this exemplary embodiment is in the range of 10-100 μsec, preferably 60 μsec, and the repeat frequency is in the range of 10-100 Hz, preferably 50 Hz.

As an alternative, it is possible to provide for main pumping current I_pump to be switched off or reduced temporarily during operation of nitrogen oxide sensor 10 and for a calibration to be performed thereby. This procedure may take place in conjunction with a digital signal processing by which a corresponding correction characteristics map is calibrated in compensation or occasionally during operation. The latter procedure may be implemented in the form of a self-learning system.

The NOx measured value acquisition module 408 shown here is used to be able to differentiate NOx values recorded within measurement time window T_Mess and compensated with respect to oxygen from the uncompensated measured values. To this end NOx measured value acquisition module 408 is triggered in time via line 406 and outputs the measured data acquired within measurement time window T_Mess via a separate output line 410 provided for that purpose.

Figure 4:
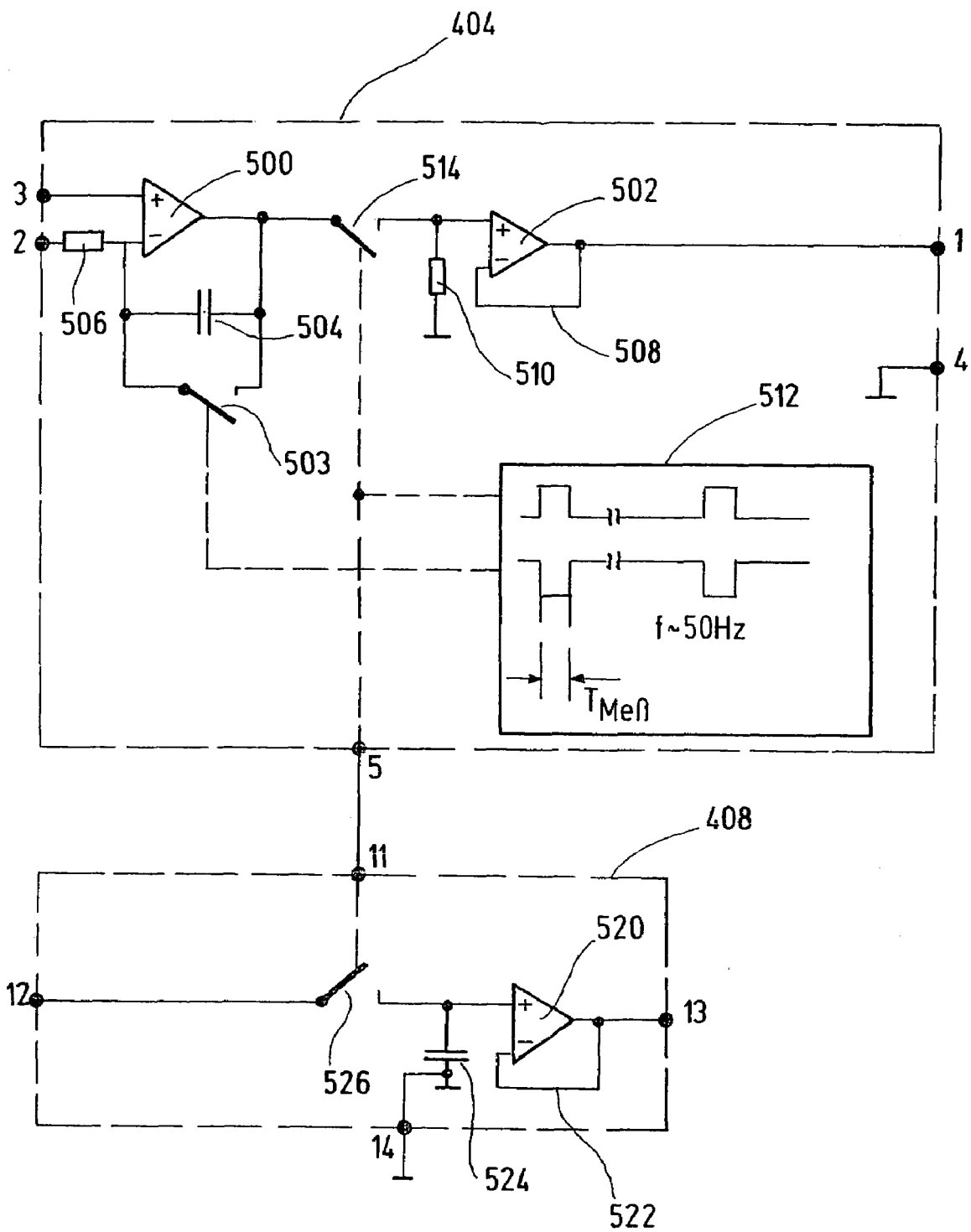
FIG. 4 shows the circuit modifications illustrated in FIG. 3 for an IPE switching off in another detail step.

The upper half of FIG. 4 shows in greater detail IPE interrupt module 404 described above and the bottom half of the figure shows in greater detail NOx measured value acquisition module 408, also described previously. The function of IPE interrupt module 404 is to briefly ramp down main pumping current I_IPE and to do so as rapidly as possible to I_IPE=I_setpoint. I_setpoint=0 or I_setpoint>0. In this ramping down, the voltage proportional to current I_IPE on the resistor of guard amplifier 54 is picked up as the actual value acquisition, the output of guard amplifier 54 being applied to terminal '2' shown in FIG. 4 and the input of guard amplifier 54 to terminal '3' shown here. The voltage difference applied to terminals '2' and '3' forms the input signal for an integral controller 500 which is wired as an interrupt regulator.

The output of integral controller 500 is connected via a switch 514 and an isolation amplifier 502 and via terminal '1' is coupled to a resistor 400 shown in FIG. 3 at summation point 38 of pumping current regulator 40. Integral controller 500 here varies the voltage at summation point 38 of pumping current regulator 40, so that pumping current I_IPE is regulated at I_setpoint after one oscillation process.

The process takes place during measurement time window T_Mess. First, switch 503 is closed and the output voltage of integral controller 500 is 0 V. This ensures that at the beginning of the regulating process, the regulator intervention will have no effect on pumping current regulator 40 and only integration in the direction predefined by I_IPE will result in a defined transient phenomenon.

As an alternative, a switch may be provided in the line between external pump electrode 30 and the regulator output of pumping current regulator 40 by which pumping current I_IPE may be set at zero immediately, i.e., without the transient phenomenon.

Furthermore, integral controller 500 may be designed so that the time constant for integration is switchable and, for example, may be switched between a relatively short first time constant and a relatively long second time constant in comparison with the first time constant. The first time constant may thus be set just before a zero crossing of pumping current I_IPE and only then switched to the second time constant, resulting in an aperiodic transient phenomenon.

Before the start of T_Mess, switch 514 is opened. Resistor 510 ensures that no voltage is supplied at summation point 38 during regular regulator operation and thus there is no effect on the current regulation. At the start of measurement time T_Mess, switch 503 is opened and switch 514 is closed so that the intervention measure of integral controller 500 is able to act on pumping current regulator 40.

NOx measured value acquisition 408 shown in the lower half of FIG. 4 has the function of detecting and storing the NOx signal at the point in time of a defined set pumping current I_IPE=I_setpoint.

The circuit configuration shown here contains a circuitry implementation of the NOx determination method depicted in FIG. 2. The signal generated thereby is used further in the IPE interrupt method according to the present invention without any technical changes in the circuit, the influence of the potentiometers (not shown), which are known in the related art and are provided separately for that purpose in the scattering current compensation shown in FIG. 3, being set at zero. The functions of the three amplifier stages 112, 114, and 116 (marked out in FIG. 3) shown in FIG. 3 therefore have practically no effect.

The NOx measured value acquisition is controlled in synchronization with integral controller 500. First a switch 526 is opened. A holding element composed of a capacitor 524 and an isolation amplifier 520 has an output voltage (terminal '13') which corresponds to the instantaneous charge state of capacitor 524. During measurement time T_Mess, switch 526 is closed so that capacitor 524 is recharged according to the input voltage applied to terminal '12'. Terminal '12' is connected to the NOx signal output shown in FIG. 3 of the analyzer circuit there.

At the end of measurement time T_Mess, switch 524 is opened again, so that the value of the NOx signal established at I_IPE=I_setpoint is stored.

Figure 5:
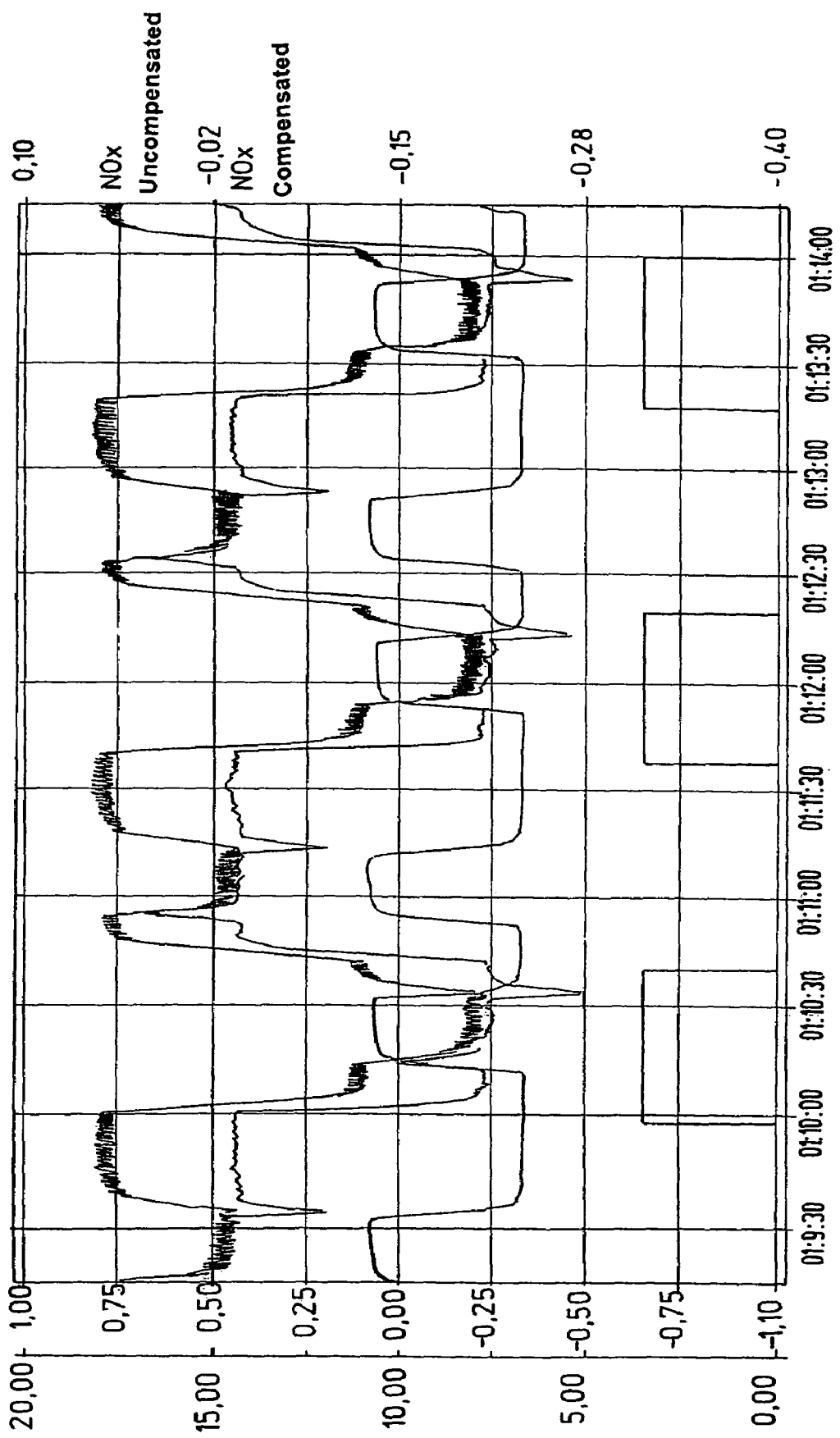
FIG. 5 shows measured curves of uncompensated NOx signals and NOx signals compensated by an IPE switching off according to the present invention for comparison.

FIG. 5 shows a comparison of measured curves of an uncompensated NOx signal and NOx signals sampled during a measurement time window T_Mess and compensated according to the present invention, namely with variable $O_2$ concentrations and variable NOx concentrations. A NOx signal recorded is plotted as a function of time in this diagram. If the value of the NOx signal is also recorded and stored just before the start of the measurement time, then the compensated and uncompensated curves may be compared.

However, it should be pointed out that the flanks of the $O_2$ concentration change are not compensated by the method according to the present invention.

Figure 6:
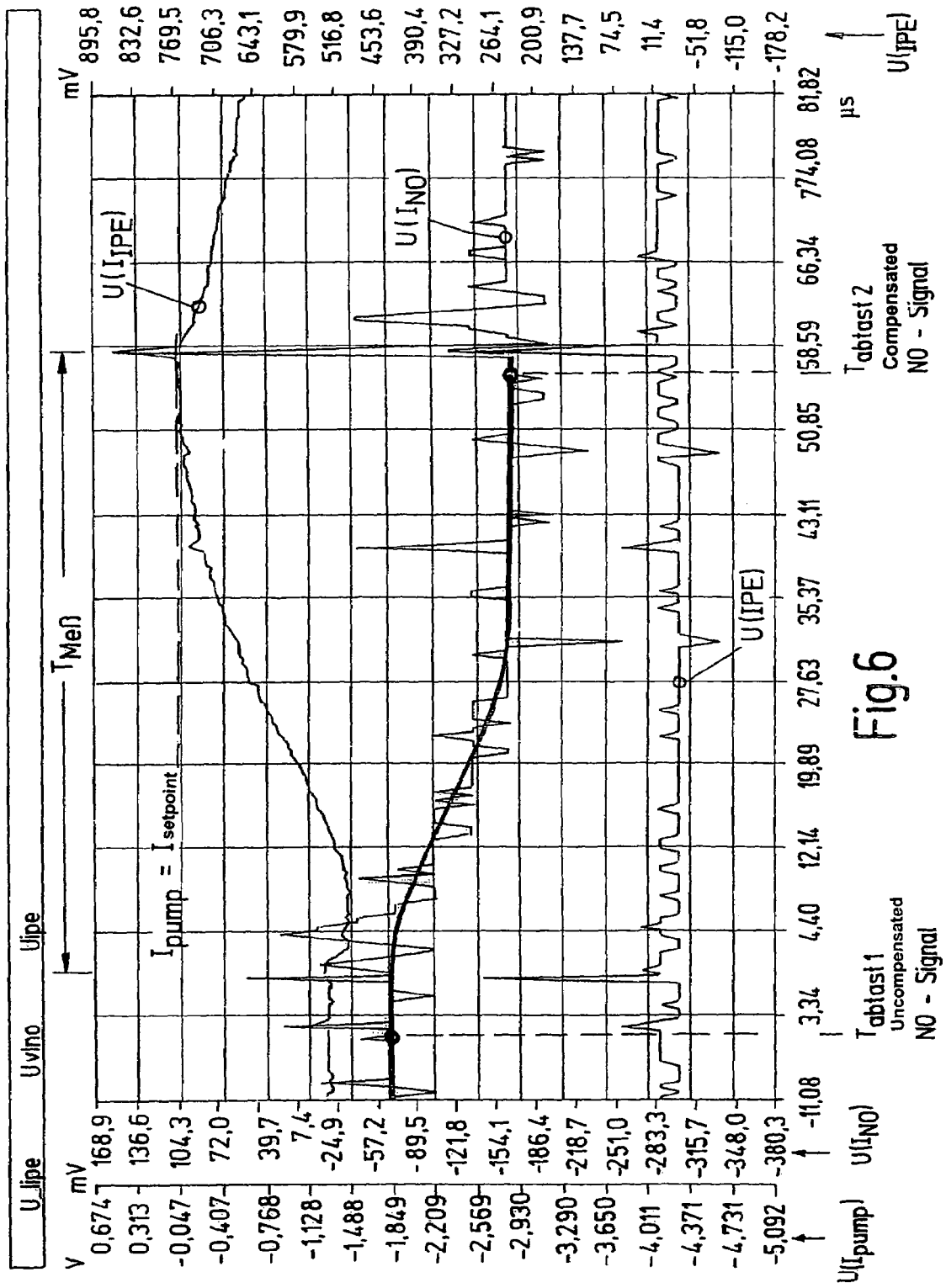
FIG. 6 shows typical signal curves of pump voltage U_IPE and NOx signal U_NOx recorded at an IPE switching off according to the present invention.

FIG. 6 shows the signal curves of U(I_IPE) and U(I_NOx) during the measurement time with the sampling points in time for the compensated and uncompensated signal, where U(I_IPE) and U(I_NO) denote the output voltages, which are applied to electrodes 'IPE' 18 and 'NO' 24, of guard amplifiers 54, 55 described above. Furthermore, U(IPE) denotes the voltage applied at the positive input of guard amplifier 54 at IPE.

What is claimed is:

1. A method for operating a nitrogen oxide sensor for determining a nitrogen oxide concentration in a gas mixture, comprising:
   applying an electric pumping voltage that induces a first pumping current between an internal pump electrode and an external pump electrode of a pumping cell, by which a constant oxygen partial pressure is set in a first test gas space by pumping oxygen in or out;
   regulating the pumping voltage so that a constant voltage value is established at electrodes of a concentration cell;
   operating an NOx-sensitive third electrode situated in a second test gas space as a second pumping cell in which a limit pumping current is established, indicating the NOx concentration;
   one of switching off and reducing in a controlled manner the first pumping current within a measurement time window; and
   recording the NOx concentration within the measurement time window.

2. The method as recited in claim 1, wherein:
   the gas mixture includes an exhaust-gas aftertreatment of a motor vehicle.

3. The method as recited in claim 1, wherein:
   the measurement time window is dimensioned so that the first pumping current flowing between the internal pump electrode and the external pump electrode subsides within the measurement time window and an increase in an oxygen concentration created due to the first pumping current being one of switched off and reduced does not reach the Nox-sensitive third electrode within the measurement time window.

4. The method as recited in claim 1, wherein:
   the first pumping current is one of switched off and reduced at a repeat frequency, whereby the repeat frequency is of such a dimension that an interference in an oxygen concentration subsides at a beginning of each subsequent one of switching off and reduction.

5. The method as recited in claim 4, wherein:
   the measurement time window is in the range of 10-100 μsec, and
   the repeat frequency is in the range of 10-100 Hz.

6. The method as recited in claim 4, wherein:
   the measurement time window is 60 μsec, and
   the repeat frequency is 50 Hz.

7. The method as recited in claim 1, wherein:
   the first pumping current is one of switched off and reduced temporarily during an operation of the nitrogen oxide sensor and a calibration is performed thereby.

8. The method as recited in claim 1, further comprising:
   setting the first pumping current one of at zero and at a constant value greater than zero during the measurement time window.

9. A circuit for operating a nitrogen oxide sensor for determining a nitrogen oxide concentration in a gas mixture, comprising:
   an arrangement for applying an electric pumping voltage that induces a first pumping current between an internal pump electrode and an external pump electrode of a pumping cell, by which a constant oxygen partial pressure is set in a first test gas space by pumping oxygen in or out;
   an arrangement for regulating the pumping voltage so that a constant voltage value is established at electrodes of a concentration cell;
   an arrangement for operating an NOx-sensitive third electrode situated in a second test gas space as a second pumping cell in which a limit pumping current is established, indicating the NOx concentration;
   an arrangement for one of switching off and reducing in a controlled manner the first pumping current within a measurement time window; and
   an arrangement for recording the NOx concentration within the measurement time window.

10. The circuit as recited in claim 9, further comprising:
    an Internal Pump Electrode (IPE) current control that sets the first pumping current one of at zero and at a constant value greater than zero during the measurement time window.

11. The circuit as recited in claim 10, wherein:
    the IPE current control sets the measurement time window in the range of 10-100 μsec and the repeat frequency in the range of 10-100 Hz.

12. The circuit as recited in claim 10, wherein:
    the IPE current control sets the measurement time window to 60 μsec and the repeat frequency to 50 Hz.

13. The circuit as recited in claim 10, further comprising:
    a connecting line;
    a two-position controller connected to the external pump electrode; and
    a switch situated in the connecting line between the external pump electrode and a regulator output of the two-position controller.

14. The circuit as recited in claim 13, further comprising:
    an integral controller connected upstream from the two-position controller and situated in the IPE current control.

15. The circuit as recited in claim 14, wherein:
    the integral controller includes an arrangement for setting a time constant for an integration.

16. The circuit as recited in claim 15, wherein:
    the integral controller is operated using a first time constant until just before a zero crossing of the pumping current and thereafter is operated using a second time constant that is larger than the first time constant.

* * * * *